(12) United States Patent
Krauss

(10) Patent No.: US 7,070,768 B2
(45) Date of Patent: Jul. 4, 2006

(54) METHOD FOR IMPARTING ARTIFICIAL TAN TO HUMAN SKIN

(75) Inventor: Achim H. Krauss, Foothill Ranch, CA (US)

(73) Assignee: Allergan, Inc., Irvine, CA (US)

( * ) Notice: Subject to any disclaimer, the term of this patent is extended or adjusted under 35 U.S.C. 154(b) by 453 days.

(21) Appl. No.: 10/672,966

(22) Filed: Sep. 25, 2003

(65) Prior Publication Data

US 2005/0069507 A1    Mar. 31, 2005

(51) Int. Cl.
    *A61Q 17/04*    (2006.01)
    *A61Q 19/00*    (2006.01)
    *A61K 8/00*    (2006.01)

(52) U.S. Cl. .......................... 424/59; 424/60; 424/400; 424/401

(58) Field of Classification Search ................. 424/59, 424/60, 400, 401
    See application file for complete search history.

(56) References Cited

U.S. PATENT DOCUMENTS

| | | | |
|---|---|---|---|
| 2,949,403 A | 8/1960 | Andreadis et al. | |
| 4,466,805 A | 8/1984 | Welters | |
| 4,708,865 A | 11/1987 | Turner | |
| 5,514,374 A | 5/1996 | Bonte et al. | |

FOREIGN PATENT DOCUMENTS

| | | |
|---|---|---|
| FR | 2850864 | 8/2004 |
| WO | 98/07438 | 2/1998 |
| WO | 99/51198 | 10/1999 |
| WO | 03/066008 | 8/2003 |
| WO | 2004/013199 | 2/2004 |

OTHER PUBLICATIONS

U.S. Appl. No. 10/345,788, filed Jan. 15, 2003, Woodward et al.

"Bimatoprost (Ophthalmic)", Medline Plus, Health Information, Jul. 24, 2001, XP002245126.

*Primary Examiner*—Shelley A. Dodson
(74) *Attorney, Agent, or Firm*—Robert J. Baran; Brent A. Johnson; Martin A. Voet

(57) ABSTRACT

The present invention relates to novel pharmaceutical compositions of bimatoprost and other cyclopentane(ene) heptan(en)oic acid amides and their use in preventing sunburn and/or providing an artificial tan to human skin.

26 Claims, No Drawings

METHOD FOR IMPARTING ARTIFICIAL TAN TO HUMAN SKIN

FIELD OF THE INVENTION

The present invention relates to the use of bimatoprost and other cyclopentane(ene) heptan(en)oic acid amides for imparting an artificial tan to human skin.

BACKGROUND OF THE INVENTION

U.S. patent application Ser. No. 10/345,788, which is hereby incorporated by reference, discloses the use of bimatoprost for enhancing hair growth. Bimatoprost, which is sold by Allergan, Inc. of Irvine, Calif., U.S.A. as Lumigan® ophthalmic solution, for treating glaucoma now has also been found as being effective to increase the growth of eyelashes when applied in the FDA approved manner. It has also been found that bimatoprost may be used for the prevention of hair graying or the conversion of gray hair of humans or other mammals to the original color of such hair as disclosed in U.S. Ser. No. 10/633,014, which was filed on Sep. 15, 2003 and is entitled: Methods for the Treatment of Gray Hair Using Cyclopentane(ene) Heptan(en)oic Acid Amides.

It has now been found that bimatoprost may be used to impart an artificial tan to human skin.

BACKGROUND OF THE INVENTION

It is generally known that certain compounds when applied topically to human skin, will produce a tanned appearance, i.e. an artificial tan. U.S. Pat. No. 4,708,865, to Turner, issued Nov. 24, 1987 describes the use of hydroalcoholic solutions of dihydroxyacetone for tanning the skin; U.S. Pat. No. 4,466,805, to Welters, issued Aug. 21, 1984 describes hair and skin coloring formulations containing dihydroxyacetone; and U.S. Pat. No. 2,949,403, to Andreadis et al., issued Aug. 16, 1960 describes artificial tanning formulations containing dihydroxyacetone in an oleaginous base. Dihydroxyacetone is believed to provide an artificial tan to human skin by its reaction with the nitrogen containing proteins of the skin.

Currently many available artificial tanning products have the disadvantage of not providing the desired control over color development of the tan. Artificial tans are often either too light or too dark, and tend to be too orange, uneven, or unnatural in appearance. Furthermore, artificial tans tend to take too long to develop, and once obtained, tend to fade too quickly and unevenly. Therefore, it would be highly desirable to provide artificial tanning products which are chemically and physically stable, which are aesthetically pleasing, and which overcome these color development limitations.

A sun-tanned appearance is a symbol of a healthy, dynamic, and active life. Yet, the damaging effects of sunlight and artificial sources of ultraviolet radiation on the skin are well documented. Furthermore these effects are cumulative and potentially serious. These effects include erythema (i.e. sunburn), skin cancer, and premature aging of the skin.

Sunscreens are the most common agents used for sun protection. However, sunscreens also have the disadvantage of preventing or greatly diminishing the cosmetically desirable tanning response. Thus, if an individual uses a sunscreen for protection from ultraviolet radiation, he or she is forced to forego a tanned appearance. Therefore, it would be highly desirable to provide protection from the harmful effects of ultraviolet radiation, and yet at the same time deliver a tanned appearance to the skin.

Furthermore, even if an individual is willing to accept the risks associated with exposure to ultraviolet radiation in order to obtain a tan, there are situations in which it may not be practical or even possible to do so because of time constraints, weather conditions, time of day, season of the year, geographic limitations, unavailability of an artificial ultraviolet radiation source, and the like. Therefore, it would be highly desirable to provide products that can deliver a tanned appearance whenever desired without the need for ultraviolet radiation.

Therefore, it would be highly desirable to provide artificial tanning products for delivering both an artificial tan and also for providing protection from ultraviolet radiation.

It is therefore an object of the present invention to provide compositions for imparting an artificial tan to human skin. A further object of the present invention is to provide stabilized compositions which are aesthetically appealing to consumers. A still further object of the present invention is to provide compositions for both imparting an artificial tan to human skin and also for protecting the skin from ultraviolet radiation. An even further object of the present invention is to provide a method for artificially tanning human skin. It is another object of the present invention to provide a method for both artificially tanning human skin and for providing protection against ultraviolet radiation.

These and other objects of this invention will become apparent in light of the following disclosure.

SUMMARY OF THE INVENTION

Bimatoprost and other cyclopentane(ene) heptan(en)oic acid amides are useful in a method of imparting an artificial tan to human skin.

This invention provides pharmaceutical compositions for topical application to impart an artificial tan to human skin comprising an effective amount of a cyclopentane(ene) heptan(en)oic acid, 2-cycloalkyl or arylalkyl compound represented by the formula I

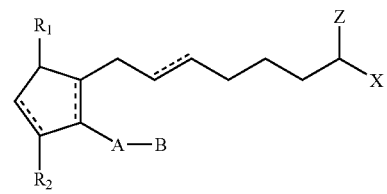

wherein the dashed bonds represent a single or double bond which can be in the cis or trans configuration, A is an alkylene or alkenylene radical having from two to six carbon atoms, which radical may be interrupted by one or more oxa radicals and substituted with one or more hydroxy, oxo, alkyloxy or akylcarboxy groups wherein said alkyl radical comprises from one to six carbon atoms; B is a cycloalkyl radical having from three to seven carbon atoms, or an aryl radical, selected from the group consisting of hydrocarbyl aryl and heteroaryl radicals having from four to ten carbon atoms wherein the heteroatom is selected from the group consisting of nitrogen, oxygen and sulfur atoms; X is —N(R4)2 wherein $R^4$ is selected from the group consisting of hydrogen, a lower alkyl radical having from one to six carbon atoms,

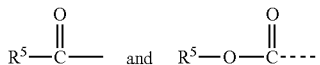

wherein R[5] is a lower alkyl radical having from one to six carbon atoms; Z is =O; one of $R_1$ and $R_2$ is =O, —OH or a —O(CO)$R_6$ group, and the other one is —OH or —O(CO)$R_6$, or $R_1$ is =O and $R_2$ is H, wherein $R_6$ is a saturated or unsaturated acyclic hydrocarbon group having from 1 to about 20 carbon atoms, or —(CH$_2$)mR$_7$ wherein m is 0 or an integer of from 1 to 10, and $R_7$ is cycloalkyl radical, having from three to seven carbon atoms, or a hydrocarbyl aryl or heteroaryl radical, as defined above in free form or a pharmaceutically acceptable salt thereof, in association with a pharmaceutical carrier.

Preferably, the compound is a cyclopentane heptanoic acid, 2-(phenyl alkyl or phenyloxyalkyl) represented by the formula II

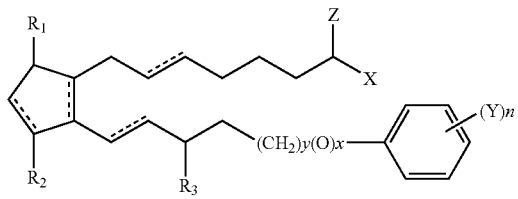

wherein y is 0 or 1, x is 0 or 1 and x and y are not both 1, Y is a radical selected from the group consisting of alkyl, halo, e.g. fluoro, chloro, etc., nitro, amino, thiol, hydroxy, alkyloxy, alkylcarboxy, halo substituted alkyl wherein said alkyl radical comprises from one to six carbon atoms, etc. n is 0 or an integer of from 1 to 3 and $R_3$ is =O, —OH or —O(CO)$R_6$ wherein $R_6$ is as defined above or a pharmaceutically acceptable salt thereof.

More preferably the compound is a compound of formula III

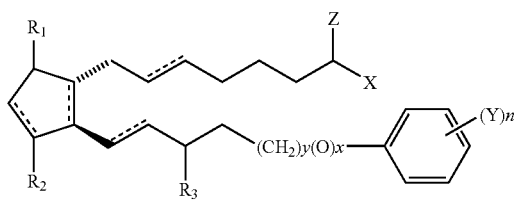

wherein hatched lines indicate α configuration, solid triangles are used to indicate β configuration.

More preferably y is 1 and x is 0 and $R_1$, $R_2$ and $R_3$ are hydroxy.

Most preferably the compound is cyclopentane N-ethyl heptanamide-5-cis-2-(3α-hydroxy-5-phenyl-1-trans-pentenyl)-3,5-dihydroxy, [1$_\alpha$,2$_\beta$,3$_\alpha$,5$_\alpha$], also known as bimatoprost.

Bimatoprost is an agent to impart an artificial tan to human skin. Bimatoprost may be administered with suitable pharmaceutical carriers and can be in solid or liquid dosage form such as tablets, capsules, powders, soft gels, solutions, suspensions, emulsions, creams or ointments. Thus, bimatoprost may be used systemically or topically; preferably topically.

Bimatoprost can be administered orally, parenterally, for example, subcutaneously, intravenously, intramuscularly, intraperitoneally, by intranasal instillation or by application to mucous membranes via an aerosol spray or by application to the scalp or skin by ointment or a cream or other suitable formulation.

The quantity of bimatoprost administered will vary depending on the patient and the mode of administration and can be any effective amount. The quantity of bimatoprost administered may vary over a wide range to provide in a unit dosage an effective amount from about 0.001 to 20 mg/kg of body weight of the patient per day to achieve the desired effect. For example, the desired affect can be obtained by consumption of a unit dosage form such as a tablet containing 1–200 mg of a cyclopentane(ene) heptan(en)oic acid amide compound of this invention taken 1–3 times daily.

These and other aspects of the invention will become apparent from the description of the invention which follows below.

DETAILED DESCRIPTION OF THE INVENTION

Some examples of representative compounds useful in the practice of the present invention include the compounds shown in Table 1:

TABLE 1 cyclopentane heptenamide-5-cis-2-(3α-hydroxy-5-phenyl-1-trans-pentenyl)-3,5-dihydroxy,[1$_\alpha$,2$_\beta$,3$_\alpha$,5$_6$α]
cyclopentane N,N-dimethylheptenamide-5-cis-2-(3α-hydroxy-5-phenyl-1-trans-pentenyl)-3,5-dihydroxy,[1$_\alpha$,2$_\beta$,3$_\alpha$,5$_\alpha$]
cyclopentane heptenylamide-5-cis-2-(3α-hydroxy-4-meta-chlorophenoxy-1-trans-pentenyl)-3,5-dihydroxy,[1$_\alpha$,2$_\beta$,3$_\alpha$,5$_\alpha$]
cyclopentane heptenylamide-5-cis-2-(3α-hydroxy-4-trifluoromethylphenoxy-1-trans-pentenyl)-3,5-dihydroxy, [1$_\alpha$,2$_\beta$,3$_\alpha$,5$_\alpha$]
cyclopentane N-isopropyl heptenamide-5-cis-2-(3α-hydroxy-5-phenyl-1-trans-pentenyl)-3,5-dihydroxy,[1$_\alpha$,2$_\beta$,3$_\alpha$,5$_\alpha$]
cyclopentane N-ethyl heptenamide-5-cis-2-(3α-hydroxy-5-phenyl-1-trans-pentenyl)-3,5 dihydroxy,[1$_\alpha$,2$_\beta$,3$_\alpha$,5$_\alpha$]
cyclopentane N-methyl heptenamide-5-cis-2-(3α-hydroxy-5-phenyl-1-trans-pentenyl)-3,5-dihydroxy,[1$_\alpha$,2$_\beta$,3$_\alpha$,5$_\alpha$]
cyclopentane heptenamide-5-cis-2-(3α-hydroxy-4-meta-chlorophenoxy-1-trans-butenyl)-3,5-dihydroxy,[1$_\alpha$,2$_\beta$,3$_\alpha$,5$_\alpha$]

One presently preferred compound for use in the practice of the present invention is cyclopentane N-ethyl heptanamide-5-cis-2-(3α-hydroxy-5-phenyl-1-trans-pentenyl)-3,5-dihydroxy, [1$_\alpha$,2$_\beta$,3$_\alpha$,5$_\alpha$], also known as bimatoprost and sold under the name of Lumigan® by Allergan, Inc., California, USA. This compound has the following structure:

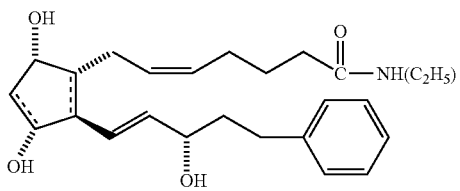

The synthesis of the compounds described above has been disclosed in U.S. Pat. No. 5,607,978. This patent also shows, particularly in Examples 1, 2, 5 and 7 that these compounds are not prostaglandins, in that they do not behave as prostaglandins in art-recognized assays for prostaglandin activity. The invention thus relates to the use of the above compounds, or prodrugs of the active compounds, for imparting an artificial tan to human skin.

In accordance with one preferred aspect of the invention, the compound is mixed with a dermatologically compatible vehicle or carrier. The vehicle which may be employed for preparing compositions of this invention may comprise, for example, aqueous solutions such as e.g., physiological salines, oil solutions or ointments.

The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

The invention is also related to dermatological compositions for topical treatment for imparting an artificial tan to human skin which comprise an effective amount of one or more compounds as defined above and a dermatologically compatible carrier. Effective amounts of the active compounds may be determined by one of ordinary skill in the art but will vary depending on the compound employed, frequency of application and desired result, and the compound will generally range from about 0.0000001 to about 50%, by weight, of the dermatological composition, preferably, from about 0.001 to about 50%, by weight, of total dermatological composition, more preferably from about 0.1 to about 30%, by weight of the composition.

The preferred pharmaceutical compositions contemplated by this invention include pharmaceutical compositions suited for topical and local action.

The term "topical" as employed herein relates to the use of a compound, as described herein, incorporated in a suitable pharmaceutical carrier, and applied at the skin of a human for exertion of local action. Accordingly, such topical compositions include those pharmaceutical forms in which the compound is applied externally by direct contact with the skin surface to be treated. Conventional pharmaceutical forms for this purpose include ointments, liniments, creams, shampoos, lotions, pastes, jellies, sprays, aerosols, and the like, and may be applied in patches or impregnated dressings depending on the part of the body to be treated. The term "ointment" embraces formulations (including creams) having oleaginous, water-soluble and emulsion-type bases, e.g., petrolatum, lanolin, polyethylene glycols, as well as mixtures of these.

Optional components which may be used in the topical formulations of this invention include sunscreens, humectants/moisturizers, emollients, emulsifiers, vitamins, preservatives, antioxidants, chelators, fragrances, pigments, opacifiers, colorings, etc. All of these optional components are more fully described in U.S. Pat. No. 5,318,774 which is hereby incorporated by reference.

The inclusion of sunscreens in the compositions used in the method of this invention is especially preferred. The most preferred sunscreens are ethylhexyl p-methoxycinnamate, octocrylene, octylsalicylate, oxybenzone and titanium dioxide.

The compounds may be applied repeatedly for a sustained period of time topically on the part of the body to be treated, for example, the face, trunk, arms, legs, etc. The dosage regimen may involve regular, such as daily, administration over a period of treatment.

For topical use on the skin, the compound can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betain, chlorhexidine, benzalkonium chloride, and the like. Various matrices for slow release delivery may also be used. Typically, the dose to be applied on the skin is in the range of about 0.1 ng to about 100 mg per day, more preferably about 1 ng to about 10 mg per day, and most preferably about 10 ng to about 1 mg per day depending on the compound and the formulation. To achieve the daily amount of medication depending on the formulation, the compound may be administered once or several times daily with or without antioxidants.

The invention is further illustrated by the following non-limiting examples:

EXAMPLE 1

A male patient (age 72) began taking bimatoprost as a tablet. After taking the medicine (oral dosage: 2.times. 100 mg per dose, 3 doses per day) for four months, it was discovered that his skin has turned to a dark brown color.

EXAMPLE 2

Topical Cream

A topical cream is prepared as follows: Tegacid and spermaceti are melted together at a temperature of 70–80° C. Methylparaben is dissolved in water and propylene glycol, polysorbate 80, and bimatoprost are added in turn, maintaining a temperature of 75–80° C. The methylparaben mixture is added slowly to the Tegacid and spermaceti melt, with constant stirring. The addition is continued for at least 30 minutes with additional stirring until the temperature has dropped to 40–45° C. Finally, sufficient water is added to bring the final weight to 1000 gm and the preparation stirred to maintain homogeneity until cooled and congealed.

The composition is applied to human skin once daily to impart an artificial tan to such skin.

EXAMPLE 3

Topical Ointment

An ointment containing 2% by weight bimatoprost is prepared as follows:

White petrolatum and wool fat are melted, strained and liquid petrolatum is added thereto. The bimatoprost, zinc oxide, and calamine are added to the remaining liquid petrolatum and the mixture milled until the powders are finely divided and uniformly dispersed. The mixture is stirred into the white petrolatum, melted and cooled with stirring until the ointment congeals.

The foregoing ointment can be applied topically to mammalian skin for converting the skin to a dark brown color, and, also, can be prepared by omitting the zinc oxide and calamine.

EXAMPLE 4

Ointment

A dermatological ophthalmic ointment containing 10% by weight bimatoprost is prepared by adding the active compound to light liquid petrolatum. White petrolatum is melted together with wool fat, strained, and the temperature adjusted to 45–50° C. The liquid petrolatum slurry is added and the ointment stirred until congealed. Suitably the ointment is packaged in 30 gm tubes.

The foregoing ointment can be applied to the skin to provide protection again UV radiation and darken the skin to a dark tan.

EXAMPLE 5

Solution

An aqueous solution containing 5%, by weight, bimatoprost is prepared as follows. Bimatoprost is dissolved in water and the resulting solution is sterilized by filtration. The solution is aseptically filled into sterile containers.

The composition so prepared can be used in the topical treatment of human skin to provide an artificial tan by application to the skin daily.

EXAMPLE 6

Lotion

A sample of bimatoprost is dissolved in a vehicle of N-methylpyrrolidone and propylene glycol. The composition can be used for application to human skin to provide protection against sunburn and impart an artificial tan.

EXAMPLE 7

Aerosol

An aerosol containing approximately 0.1% by weight bimatoprost is prepared by dissolving the bimatoprost in absolute alcohol. The resulting solution filtered to remove particles and lint. This solution is chilled to about minus 30° C. To the solution is added a chilled mixture of dichlorodifluoromethane and dichlorotetrafluoroethane. Thirteen ml plastic-coated amber bottles are cold filled with 11.5 gm each of the resulting solution and capped.

The composition can be sprayed on the skin daily to prevent sunburn.

EXAMPLE 8

Dusting Powder

A powder of the compound bimatoprost is prepared by mixing in dry form with talcum powder at a weight/weight ratio of 1:10. The powdered mixture is dusted on the top of the head to provide protection against sun burning of the scalp.

EXAMPLE 9

Related Compounds

Following the procedure of the preceding Examples, compositions are similarly prepared substituting an equimolar amount of a compound of Table 1 for the bimatoprost disclosed in the preceding Examples. Similar results are obtained.

The present invention is not to be limited in scope by the exemplified embodiments, which are intended as illustrations of individual aspects of the invention. Indeed, various modifications for the invention in addition to those shown and described herein will be come apparent to those skilled in the art from the foregoing description. Such modifications are intended to fall within the scope of the appended claims.

I claim:
1. A method of imparting an artificial tan to the skin of a human which comprises administering to said human a pharmaceutical composition comprising an effective amount of a compound represented by formula I

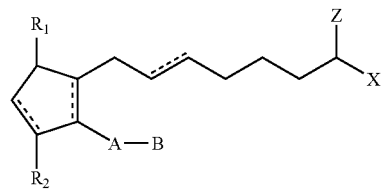

wherein the dashed bonds represent a single or double bond which can be in the cis or trans configuration, A is an alkylene or alkenylene radical having from two to six carbon atoms, which radical may be interrupted by one or more oxa radicals and substituted with one or more hydroxy, oxo, alkyloxy or akylcarboxy groups wherein said alkyl radical comprises from one to six carbon atoms; B is a cycloalkyl radical having from three to seven carbon atoms, or an aryl radical, selected from the group consisting of hydrocarbyl aryl and heteroaryl radicals having from four to ten carbon atoms wherein the heteroatom is selected from the group consisting of nitrogen, oxygen and sulfur atoms; X is $-N(R^4)_2$ wherein $R^4$ is selected from the group consisting of hydrogen, a lower alkyl radical having from one to six carbon atoms,

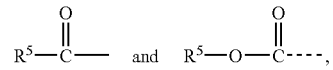

wherein $R^5$ is a lower alkyl radical having from one to six carbon atoms; Z is $=O$; one of $R_1$ and $R_2$ is $=O$, $-OH$ or a $-O(CO)R_6$ group, and the other one is $-OH$ or $-O(CO)R_6$, or $R_1$ is $=O$ and $R_2$ is H, wherein $R_6$ is a saturated or unsaturated acyclic hydrocarbon group having from 1 to about 20 carbon atoms, or $-(CH_2)mR_7$ wherein m is 0 or an integer of from 1 to 10, and $R_7$ is cycloalkyl radical, having from three to seven carbon atoms, or a hydrocarbyl aryl or heteroaryl radical, as defined above or a pharmacologically acceptable acid addition salt thereof.

2. The method of claim 1 wherein the concentration of the compound applied is from 0.0000001% to 50% by weight of the composition.

3. The method of claim 1 wherein the compound is a compound of formula III

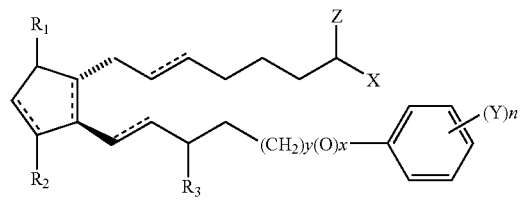

wherein y is 0 or 1, x is 0 or 1 and x and y are not both 1, Y is a radical selected from the group consisting of alkyl, halo, nitro, amino, thiol, hydroxy, alkyloxy, alkylcarboxy, halo substituted alkyl wherein said alkyl radical comprises from one to six carbon atoms, n is 0 or an integer of from 1 to about 3 and $R_3$ is =O, —OH or —O(CO)$R_6$ wherein $R_6$, hatched lines indicate α configuration and solid triangles are used to indicate β configuration.

4. The method of claim 3 wherein the compound is bimatoprost or a pharmaceutically acceptable salt thereof.

5. The method of claim 1 wherein the compound of formula I is applied systemically.

6. The method of claim 1 wherein the compound of formula I is applied topically.

7. The method of claim 1 wherein the compound of formula I is applied by aerosol.

8. The method of claim 1 wherein the compound of formula I is applied as a cream.

9. The method of claim 1 wherein the compound of formula I is applied as a lotion.

10. The method of claim 1 wherein the compound of formula I is applied as a solution.

11. A method for providing both an artificial tan to human skin and protecting human skin from the effects of ultraviolet radiation which comprises administering to human skin a pharmaceutical composition comprising an effective amount of a compound represented by formula I

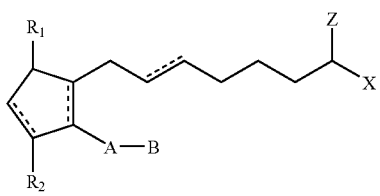

wherein the dashed bonds represent a single or double bond which can be in the cis or trans configuration, A is an alkylene or alkenylene radical having from two to six carbon atoms, which radical may be interrupted by one or more oxa radicals and substituted with one or more hydroxy, oxo, alkyloxy or akylcarboxy groups wherein said alkyl radical comprises from one to six carbon atoms; B is a cycloalkyl radical having from three to seven carbon atoms, or an aryl radical, selected from the group consisting of hydrocarbyl aryl and heteroaryl radicals having from four to ten carbon atoms wherein the heteroatom is selected from the group consisting of nitrogen, oxygen and sulfur atoms; X is —N(R$_4$)$_2$ wherein R$^4$ is selected from the group consisting of hydrogen, a lower alkyl radical having from one to six carbon atoms,

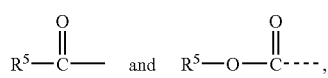

wherein $R^5$ is a lower alkyl radical having from one to six carbon atoms; Z is =O; one of $R_1$ and $R_2$ is =O, —OH or a —O(CO)$R_6$ group, and the other one is —OH or —O(CO)$R_6$, or $R_1$ is =O and $R_2$ is H, wherein $R_6$ is a saturated or unsaturated acyclic hydrocarbon group having from 1 to about 20 carbon atoms, or —(CH$_2$)m$R_7$ wherein m is 0 or an integer of from 1 to 10, and $R_7$ is cycloalkyl radical, having from three to seven carbon atoms, or a hydrocarbyl aryl or heteroaryl radical, as defined above or a pharmacologically acceptable acid addition salt thereof.

12. The method of claim 11 wherein the concentration of the compound applied is from 0.0000001% to 50% by weight of the composition.

13. The method of claim 11 wherein the compound is a compound of formula III

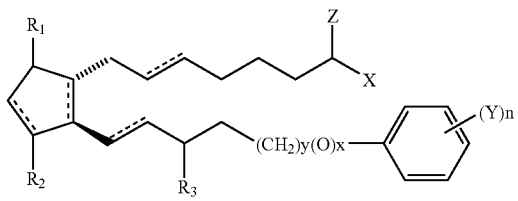

wherein y is 0 or 1, x is 0 or 1 and x and y are not both 1, Y is a radical selected from the group consisting of alkyl, halo, nitro, amino, thiol, hydroxy, alkyloxy, alkylcarboxy, halo substituted alkyl wherein said alkyl radical comprises from one to six carbon atoms, n is 0 or an integer of from 1 to about 3 and $R_3$ is =O, —OH or —O(CO)$R_6$ wherein $R_6$, hatched lines indicate α configuration and solid triangles are used to indicate β configuration.

14. The method of claim 13 wherein the compound is bimatoprost or a pharmaceutically acceptable salt thereof.

15. The method of claim 11 wherein the compound of formula I is applied systemically.

16. The method of claim 11 wherein the compound of formula I is applied topically.

17. The method of claim 11 wherein the compound of formula I is applied by aerosol.

18. The method of claim 11 wherein the compound of formula I is applied as a cream.

19. The method of claim 11 wherein the compound of formula I is applied as a lotion.

20. The method of claim 1 wherein the compound of formula I is applied as a solution.

21. An artificial tanning composition for providing both an artificial tan to human skin and protecting human skin from the effects of ultraviolet radiation which comprises a pharmaceutical composition comprising an effective amount of a compound represented by formula I

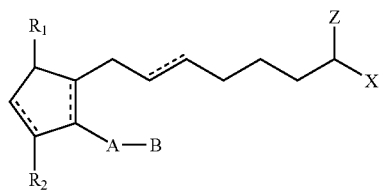

wherein the dashed bonds represent a single or double bond which can be in the cis or trans configuration, A is an alkylene or alkenylene radical having from two to six carbon atoms, which radical may be interrupted by one or more oxa radicals and substituted with one or more hydroxy, oxo, alkyloxy or akylcarboxy groups wherein said alkyl radical comprises from one to six carbon atoms; B is a cycloalkyl radical having from three to seven carbon atoms, or an aryl radical, selected from the group consisting of hydrocarbyl aryl and heteroaryl radicals having from four to ten carbon atoms wherein the heteroatom is selected from the group consisting of nitrogen, oxygen and sulfur atoms; X is —$N(R^4)_2$ wherein $R^4$ is selected from the group consisting of hydrogen, a lower alkyl radical having from one to six carbon atoms,

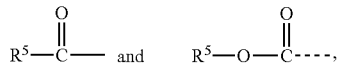

wherein $R^5$ is a lower alkyl radical having from one to six carbon atoms; Z is =O; one of $R_1$ and $R_2$ is =O, —OH or a —$O(CO)R_6$ group, and the other one is —OH or —$O(CO)R_6$, or $R_1$ is =O and $R_2$ is H, wherein $R_6$ is a saturated or unsaturated acyclic hydrocarbon group having from 1 to about 20 carbon atoms, or —$(CH_2)mR_7$ wherein m is 0 or an integer of from 1 to 10, and $R_7$ is cycloalkyl radical, having from three to seven carbon atoms, or a hydrocarbyl aryl or heteroaryl radical, as defined above or a pharmacologically acceptable acid addition salt thereof and a sunscreen.

22. The composition of claim 21 wherein the concentration of said compound is from 0.0000001% to 50% by weight of the composition.

23. The composition of claim 21 wherein the compound is a compound of formula III

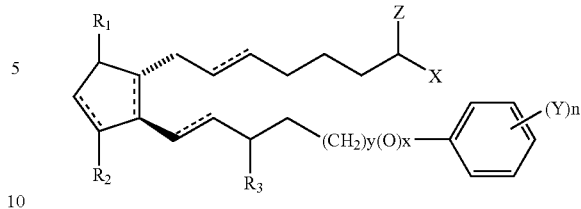

wherein y is 0 or 1, x is 0 or 1 and x and y are not both 1, Y is a radical selected from the group consisting of alkyl, halo, nitro, amino, thiol, hydroxy, alkyloxy, alkylcarboxy, halo substituted alkyl wherein said alkyl radical comprises from one to six carbon atoms, n is 0 or an integer of from 1 to about 3 and $R_3$ is =O, —OH or —$O(CO)R_6$ wherein $R_6$, hatched lines indicate α configuration and solid triangles are used to indicate β configuration.

24. The composition of claim 23 wherein said compound is bimatoprost or a pharmaceutically acceptable salt thereof.

25. The composition of claim 21 wherein said sunscreen is selected from the group consisting of ethylhexyl p-methoxycinnamate, octocrylene, octylsalicylate, oxybenzone and titanium dioxide.

26. The composition of claim 24 wherein said sunscreen is selected from the group consisting of ethylhexyl p-methoxycinnamate, octocrylene, octylsalicylate, oxybenzone and titanium dioxide.

* * * * *